United States Patent [19]

Braham et al.

[11] Patent Number: 5,705,389

[45] Date of Patent: Jan. 6, 1998

[54] OLIGONUCLEOTIDES THAT INHIBIT PRODUCTION OF α-TUMOR NECROSIS FACTOR

[75] Inventors: Abdel Karim Braham, Saint Denis; Pierre Smets, Villennes sur Seine; René Zalisz, Menucourt, all of France

[73] Assignee: Roussel Uclaf, France

[21] Appl. No.: 342,338

[22] Filed: Nov. 18, 1994

Related U.S. Application Data

[63] Continuation of Ser. No. 39,924, Mar. 29, 1993, abandoned, which is a continuation of Ser. No. 865,206, Apr. 8, 1992, abandoned, which is a continuation of Ser. No. 570,215, Aug. 21, 1990, abandoned.

[30] Foreign Application Priority Data

Aug. 23, 1989 [FR] France .................... 89-11171

[51] Int. Cl.$^6$ .............. C12N 5/10; C07H 21/02; C12Q 1/68; A61K 31/70
[52] U.S. Cl. .............. 435/375; 435/6; 536/24.5; 536/23.1; 536/24.3; 536/24.32; 536/24.33; 536/25.31; 536/25.34
[58] Field of Search .............. 514/44, 2; 536/23.1, 536/24.3, 24.31, 24.33, 24.5; 435/91.1, 172.3, 91.2, 320.1, 240.2, 91.31, 375; 424/93.21

[56] References Cited

PUBLICATIONS

Rojanasakul, Adv. Drug. Del. Rev., 18:115–131, 1996.
Stein et al, Science, 261, 1993, 1004–1012.
Uhlmann et al, Chemical, Reviews, 90(4), 1990, 544–584.
Marmenout, et al, Eur. J. Biochemistry, 152, 515–522, 1985.
Melton, Proc. Natl. Acad. Sci, U.S.A, 82, 144–148, 1985.
Zon, Pharmaceutical Res., 5(9), pp. 539–549, 1988.

*Primary Examiner*—Charles C.P. Rories
*Attorney, Agent, or Firm*—Bierman, Muserlian & Lucas

[57] ABSTRACT

A sequence of anti-direction, anti-messenger RNA oligonucleotides of α-TNF characterized in that it possesses the structure of the formula

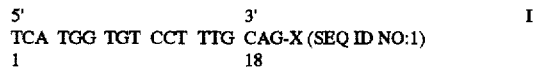

wherein X is hydrogen, or a sequence of 1 to 17 oligonucleotides in free form, in alkylated form, in sulfurated form or in the form of a poly L-lysine derivative useful for stopping the production of α-TNF.

9 Claims, No Drawings

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 19
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: IN THE SPECIFICATION X=N, X IS
            HYDROGEN, OR A SEQUENCE OF 1 TO 17 OLIGONUCLEOTIDES
            IN FREE FORM, IN ALKYLATED FORM, IN SULFURATED FORM
            OR IN THE FORM OF A POLY-L-LYSINE DERIVATIVE ( x i ) SEQUENCE DESCRIPTION: SEQ ID NO: 1:

TCATGGTGTC CTTTGCAGN ( 2 ) INFORMATION FOR SEQ ID NO: 2:

```
( i ) SEQUENCE CHARACTERISTICS:
    ( A ) LENGTH: 17
    ( B ) TYPE: NUCLEIC ACID
    ( C ) STRANDEDNESS: SINGLE
    ( D ) TOPOLOGY: UNKNOWN ( i i ) MOLECULE TYPE: OLIGONUCLEOTIDE ( x i ) SEQUENCE DESCRIPTION: SEQ ID NO: 2:

CCTCATGCTT TCAGTAG                                                          17

( 2 ) INFORMATION FOR SEQ ID NO: 3:

( i ) SEQUENCE CHARACTERISTICS:
        ( A ) LENGTH: 20
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( x i ) SEQUENCE DESCRIPTION: SEQ ID NO: 3:

TCATGGTGTC CTTTGCAGCC                                                       20

( 2 ) INFORMATION FOR SEQ ID NO: 4:

( i ) SEQUENCE CHARACTERISTICS:
        ( A ) LENGTH: 18
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( x i ) SEQUENCE DESCRIPTION: SEQ ID NO: 4:

TCATGGTGTC CTTTGCAG                                                         18

( 2 ) INFORMATION FOR SEQ ID NO: 5:

( i ) SEQUENCE CHARACTERISTICS:
        ( A ) LENGTH: 35
        ( B ) TYPE: NUCLEIC ACID
        ( C ) STRANDEDNESS: SINGLE
        ( D ) TOPOLOGY: UNKNOWN ( i i ) MOLECULE TYPE: OLIGONUCLEOTIDE ( x i ) SEQUENCE DESCRIPTION: SEQ ID NO: 5:

TCATGGTGTC CTTTGCAGCC TCATGCTTTC AGTAG                                      35
```

OLIGONUCLEOTIDES THAT INHIBIT PRODUCTION OF α-TUMOR NECROSIS FACTOR

PRIOR APPLICATIONS

This application is a continuation of U.S. patent application Ser. No. 08/039,924 filed Mar. 29, 1993, now abandoned, which is a continuation of U.S. patent application Ser. No. 07/865,206 filed Apr. 8, 1992, now abandoned, which is a continuation of U.S. patent application Ser. No. 07/570,215 filed Aug. 21, 1990, now abandoned.

STATE OF THE ART

It is known that TNF (Tumor Necrosis Factor) secreted by macrophages is responsible for absolute metabolic disasters that can create an infectious endotoxinic shock. In seeking to stop the source of TNF production, the research of the sequences of anti-direction, anti-messenger RNA oligonucleotides which can thus stop the production of TNF has been conducted. Pertinent prior art includes PCT aplication WO.A. 806,625 and WO.A 8,604,606 and Nucleic Acids Research, Vol. 13 No. 17 (1985), p. 6361 to 6373.

OBJECTS OF THE INVENTION

It is an object of the invention to provide novel sequences of anti-direction, anti-messenger RNA oligonucleotides of α-TNF and their preparation.

It is another object of the invention to provide novel compositions and a novel method of stopping the production of α-TNF.

These and other objects and advantages of the invention will become obvious from the following detailed description.

THE INVENTION

The novel sequence of the invention of anti-direction, anti-messenger RNA oligonucleotides of α-TNF is characterized in that it possesses the structure of the formula

```
5'                              3'                      I
TCA TGG TGT CCT TTG CAG  - X (SEQ ID NO: 1)
1                        18
``` wherein X is hydrogen, or a sequence of 1 to 17 oligonucleotides in free form, in alkylated form, in sulfurated form or in the form of a poly-L-lysine derivative.

In formula I, the sequence of 1 to 17 oligonucleotides means any sequence of adenine and guanine (purine bases) and cytosine and thymine (pyrimidine bases). Alkylated form means alkylated derivatives with an alkyl on the phosphate and especially methyl, ethyl or propyl which groups may be present on all or some of the phosphate groups. Sulfurated forms means sulfurated derivatives of the phosphate, especially thioates and dithioates which can be present on, some or all of the phosphate groups.

Examples of sequences of oligonucleotides of formula I are those wherein X is hydrogen or all or part of the sequence of the formula

```
    5'                        3'              I_A
    -CC TCA TGC TTT CAG TAG (SEQ ID NO: 2)
    19                    35
``` in free form, in alkylated form, in sulfurated form or in the form of a poly L-lysine derivative.

Among the latter, there are preferred the oligonucleotide sequences of formula I in which X is a hydrogen atom, a sequence of formula —CC or the sequence of formula I_A, in free form, in alkylated form, in sulfurated form or in the form of a poly L-lysine derivative, and especially the following sequences:

```
5'                              3'
TCA TGG TGT CCT TTG CAG CC (SEQ ID NO: 3)
1                       20

5'                           3'
TCA TGG TGT CCT TTG CAG (SEQ ID NO: 4)
1                      18

5'                                                       3'
TCA TGG TGT CCT TTG CAG CC TCA TGC TTT CAG TAG (SEQ ID NO: 5)
1                                                       35
```

The novel process of the invention for the preparation of oligonucleotides of formula I comprises immobilizing the first nucleotide in position 3' of the chain on a support to form of the formula

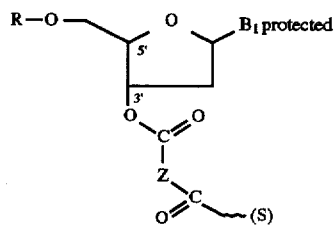

wherein S is the support, Z is a hydrocarbon of 2 to 20 carbon atoms, $B_1$ is a purine or pyrimidine base corresponding to the first nucleotide, the amine function of which is protected and R is a protective group, deblocking the hydroxyl in position 5' with an acid reagent to obtain a compound of the formula

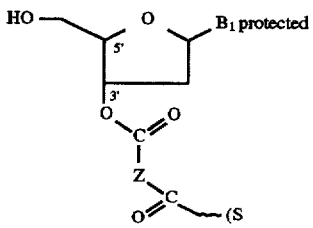

in which S, Z and $B_1$ have the above definitions, reacting the latter with the monomer of the second nucleotide of the formula

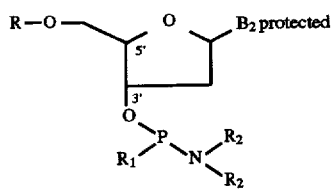

IV

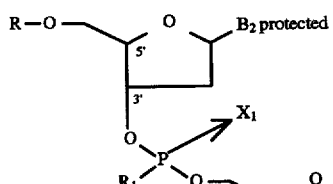

VI in which R has the above meaning, $B_2$ is a purine or pyrimidine base corresponding to the second nucleotide, the amine function of which is protected, $R_1$ is alkyl or $-OR'_1$ or $SR'_1$ wherein $R'_1$ is a protector group, and $R_2$ is a protector group to obtain a product of the formula

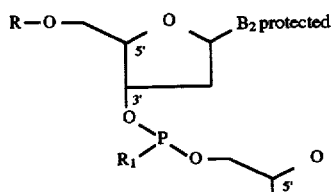

V wherein S, R, $R_1$, $B_1$, $B_2$ and Z have the above definitions and $X_1$ is oxygen or sulfur, then, a new ring is produced with this product of formula VI as from the product of formula II and the monomer of a new nucleotide until the desired chain formation is obtained to obtain finally a product of the formula wherein S, R, $R_1$, $B_1$ and $B_2$ have the above definitions, oxidizing the product of formula V to obtain a product of the formula

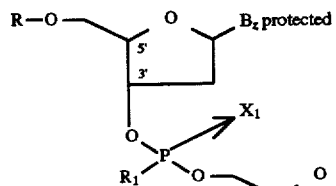
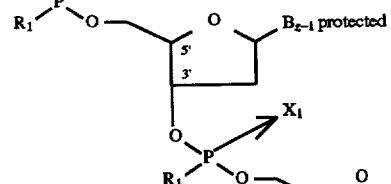
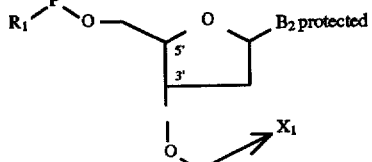
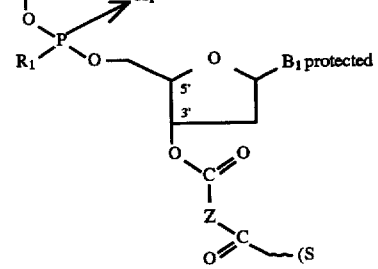

wherein S, R, $R_1$, $B_1$, $B_2$, $X_1$ and Z have the above definitions and $B_z$ is the last nucleotide of the sequence, then deprotecting the oligonucleotide and separation from the support to obtain the product of formula I which is purified.

In the preferred operating conditions of the process, the deblocking of the hydroxyl in position 5' of the product of formula II is effected with an acid reagent such as acetic acid or di- or trichloroacetic acid, the coupling reaction of the product of formula III with the product of formula IV is activated with tetrazole in acetonitrile, the oxidation of the phosphite of formula V into the phosphate of formula VI is effected with iodine in solution of a water/lutidine/tetrahydrofuran mixture or in a water/pyridine/tetrahydrofuran mixture, the oxidation of the phosphite of formula V to obtain the sulfurated form VI is effected with sulfur in solution in a mixture of carbon sulfide, anhydrous pyridine and anhydrous triethylamine, at the end of the synthesis, the deprotection of the terminal hydroxyl group in position 5' is effected with an acid such as acetic acid or di- or trichloroacetic acid and the deprotection of the oligonucleotide of formula VII is effected with concentrated ammonium hydroxide by moderately heating the reaction medium.

For the operation of the process described above, the automatic synthesizer "Applied Biosystems, Model 381A" is preferably used.

In the process of the invention, the support S is a solid support which can be constituted of silica or porous glass and can also be used the supports described in European Patent No. 0,208,599.

According to the invention, Z is a hydrocarbon —$(CH_2)_n$— in which n is an integer from 2 to 20. Products in which Z is —$(CH_2)_2$— are preferably used.

In the formulae II to VII, the bases $B_1$, $B_2$ . . . . $B_z$ are purine or pyrimidine bases, the amine functions of which are protected. Examples of the protector groups are benzoyl or isobutyryl. In the case of adonine and cytosine, benzoyl is preferably used. In the case of guanine, isobutyryl is preferably used.

The protector group R of the hydroxyl function in position 5' is, for example, trityl, monomethoxytrityl, dimethoxytrityl or pixyl.

The protector group of $R'_1$ of the hydroxyl functions of the phosphate groups can be for example, methyl, cyanoethyl, ortho or para-chlorophenyl and the cyanoethyl group is preferably used. The protector group of $R_2$ can be alkyl such as methyl, ethyl, isopropyl or morpholino or piperidino with isopropyl preferably used.

During the operation of the process, the fraction of the product of formula III which has not reacted is immediately converted into an ester to avoid the formation of a bad sequence for the following coupling. This reaction of "capping" is effected preferably with acetic anhydride in a lutidine/tetrahydrofuran mixture and is catalyzed by 4-dimethylamino-pyridine or by methylimidazole.

The poly L-lysine derivatives of the oligonucleotide sequences can be prepared by a process characterized in that a product of formula

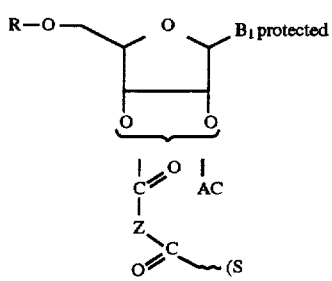

VIII wherein S, Z, R, $B_1$ have the above definitions is reacted with product of formula IV to obtain a product of the formula

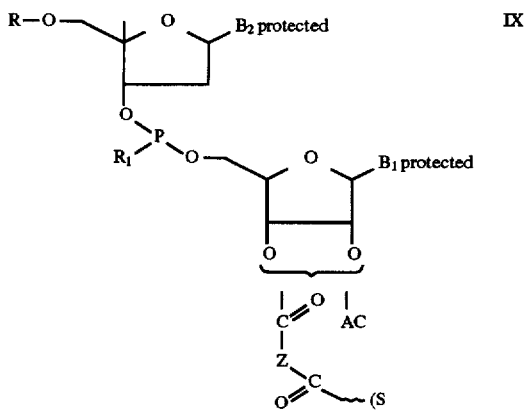

IX wherein S, R, Z, $R_1$, $B_1$ and $B_2$ have the above definitions followed by oxidizing and eliminating the support and the activating group to obtain a product of the formula

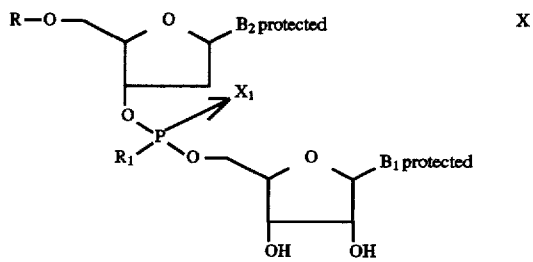

X wherein R, $R_1$, $B_1$ and $D_2$ have the above definitions, $X_1$ is oxygen or sulfur, the terminal ribose is oxidized then reacted with L-lysine in a reducing medium to obtain the product of the formula

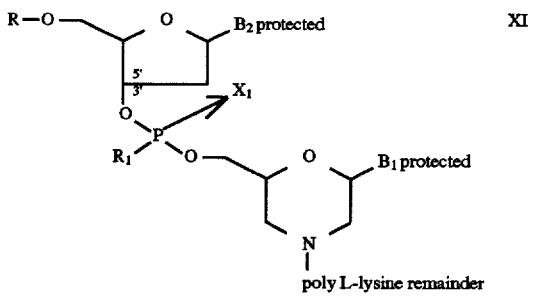

XI wherein R, $R_1$, $B_1$, $B_2$ and $X_1$ have the above definitions and then the synthesis is continued as from the product of formula VI.

The poly L-lysine derivatives can be prepared by a process similar to the process described by LEONETTI et al. GENE, Vol. 72 (1988), p. 323 to 332.

The novel compositions for halting the production of -TNF are comprised of an amount of a sequence of formula I sufficient to halt production of α-TNF and an inert carrier or excipient. The compositions may be in the form of tablets, dragees, gelules, capsules, granules, suppositories, injectable solutions or suspensions and aerosols.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions, due to the fact that they possess the capability of stopping the production of α-TNF by the cells by attaching themselves specifically to the target messenger RNA at the level of the sequence [166 to 185] which is found astride the codon AUG, are useful for the treatment of infectious endotoxinic shocks of all origins and of all the pathological conditions connected with a hypersecretion of α-TNF.

The novel method of the invention of halting the production of α-TNF in warm-blooded animals, including humans, comprises administering to warm-blooded animals an amount of a sequence of formula I sufficient to halt production of α-TNF. The sequence may be administered orally, rectally, parenterally or topically and the usual daily dose is 0.0133 μg to 0.4 mg/kg depending on the condition treated, the specific sequence and the method of administration.

In the following examples there are described several preferred embodiments of the invention to illustrate the invention. However, it should be understood that the invention is not intended to be specific embodiments.

EXAMPLE 1

Sequence (d) TCA TGG TGT CCT TTG CAG (SEQ ID NO:4) (18 "mer" anti-αTNF) in free form An "Applied Biosystems Model 381 A" automatic synthesizer was used and the apparatus was loaded with all the necessary reagents. The products of formula IV were dissolved in acetonitrile under a light argon pressure which enabled them to be delivered automatically by the opening of electro-valves as and when required. The nucleotide sequence to be synthesized was recorded and the quantity of product on which one desired to work was indicated. The final detritylation was optionally programmed to recover the product of formula I in hydroxylated form or in tritylated form in position 5.

A small previously filled column containing the functionalized support II was placed on the apparatus (CPG porous glass support). The synthesis was then carried out from start to finish without manual intervention. The detritylation solutions were recovered automatically at each stage in a fraction collector coupled to the apparatus so that the yields at each stage could be known.

Reagents

All the reagents used must be very pure. The 4 phosphoramidites of formula IV ($B_2$=adenine, cytosine, guanine or thymine) were packed into small flasks and it was sufficient to add the necessary quantity of solvent before introducing them into the apparatus.

The other solutions introduced into the apparatus were the following: a) 4% tetrazole in acetonitrile for the coupling activator, b) acetic anhydride/lutidine/tetrahydrofuran 1/1/8 on the one hand and dimethylaminopyridine/tetrahydrofuran 7/93 on the other hand mixed in situ for the "capping" reaction, c) Iodine/water/lutidine/tetrahydrofuran 3/2/2/93 for the oxidation of the phosphite of formula V into phosphate of formula VI, d) 2% trichloroacetic acid in dichloromethane for the detritylation reaction and e) pure acetonitrile for the dissolution of the phosphoramidites.

Method

The reaction was effected on 0.95 micromole and the product was detritylated in the apparatus at the end of the synthesis. The yield of crude product from the synthesis was 79%. The deblocking of the product of formula VII was effected in the following way:

1–28% ammonium hydroxide for one hour at ambient temperature and

2—saturated ammonium hydroxide at 60° C. for 5 hours.

Purification

1—Desalinization on NAP 10 (Pharmacia) Sephadex G50® column.

2—HPLC on Partisil 10 SAX® column, gradient of 50 to 99% of solvent A in the mixture A+B over 20 minutes.

A=buffer of 0.3M phosphate/$CH_3CN$ 7/3 pH 6.2

B=buffer of $10^{-3}$M phosphate /$CH_3CN$ 7/3 pH 6.2 supply rate 2 ml/min,

3—Desalinization on NAP 25 (Pharmacia) Sephadex G50® column.

Analysis of purified product

HPLC on Partisil 10 SAX® same conditions as above, RT=13.92 min.

HPLC on inverse phase microbondapack C18® gradient 8.4 to 15% of $CH_3CN$ in $10^{-2}$M triethylammonium acetate, pH 5.5, over 20 minutes, supply rate 2 ml/min. TR=12.13 min.

Finally 0.125 micromolo of pure product was obtained in a yield of 13%.

EXAMPLE 2

Sequence (d) TCA TGG TGT CCT TTG CAG (SEQ ID NO:4) (18 "mer" anti-αTNF) all in thioate form Using the procedure of Example 1, but replacing the oxidation cycle using iodine by an oxidation stage using sulfur for 450 seconds, the desired product mentioned was obtained. The solution of iodine/water/lutidine/tetrahydrofuran was replaced by a solution of: 3 g of sulfur, 28.5 ml of carbon sulfide, 28.5 ml of anhydrous pyridine and 3 ml of anhydrous triethylamine.

In the case of an oxidation with sulfur, it was indispensable to rinse the column before and after oxidation, washing repeatedly with a solution of carbon sulfide in pyridine 1/1 to remove any sulfur residue. For the rest, the method remained unchanged. The *Yield for synthesis* on 1.24 micromole was 56.5%.

Deblocking 1 28% ammonium hydroxide for one hour at ambient temperature

2—saturated ammonium hydroxide for one night at 50° C.

Purification

1—desalinization NAP 25 (Sephadex)® eluant $H_2O$.

2—HPLC control microbondapack C18®RT=24.46

Gradient of 30 to 50% of A over 20 min., supply rate 2 ml/min.

A=triethylammonium acetate $10^{-2}$M/l., pH 5.5/$CH_3CN$ 7/3

B=triethylammonium acetate $10^{-2}$M/l., pH 5.5

Pure product yield was 40.3%

EXAMPLE 3

Sequence (d) TCA TGG TGT CCT TTG CAG CC (SEQ ID NO:3) (20 "mere" anti-αTNF) in free form Using the procedure of Example 1, the desired product was obtained.

EXAMPLE 4

Sequence (d) TCA TGG TGT CCT TTG CAG CC TCA TGC TTT CAG TAG (SEQ ID NO: 5) "mere" anti-αTNF) in free form Using the procedure of Example 1, the desired product was obtained.

EXAMPLE 5

An injectable solute was prepared containing 10 micrograms of the product of Example 1 and sufficient sterile aqueous excipient for a volume of 2 ml.

EXAMPLE 6

Tablets were prepared containing 20 micrograms of the product of Example 2 and sufficient excipient of lactoses, starch, talc and magnesium stearate for a tablet of 100 mg.

EXAMPLE 7

An injectable solute was prepared containing 10 micrograms of the product of Example 3 and sufficient sterile aqueous excipient for a volume of 2 ml.

STUDY OF THE OLIGONUCLEOTIDE SEQUENCE PREPARED IN EXAMPLE 3

1—Biological test 1.1—Incubation of the human monocytes ($4\times10^{-6}$ cells) with 6 micromoles of anti-direction oligonucleotides in the 4 forms for 3 hours.

1.2—Then addition of the LPS (10 micrograms/ml) and the INF ($5\times10^3$ µ/ml).

1.3—Incubation for 18 hours, 1.4—Taking up the culture supernatant.

1.5—Addition of this supernatant to the cells sensitive to lysis by TNF (L. 929) for 24 hours.

1.6—Measurement of the cellular viability by colorimetry with crystal violet.

2—Immunological test 2.1—Incubation of the human monocytes ($4\times10^6$ cells) with 6 micromoles of anti-direction oligonucleotides in the 4 forms for 3 hours.

2.2—Next, addition of the LPS (10 micrograms/ml) and the INF ($5\times10^3$ µ/ml) for the stimuation of the TNF production.

2.3—Incubation for 18 hours.

2.4—Taking up the culture supernatant.

2.5—Forming a coating with this culture supernatant.

2.6—Addition of anti-TNF antibody marked with iodine (for RIA) or wish an enzyme (for ELISA).

2.7—Incubation for 3 hours.

2.8—Readings a) add the enzyme substrate (ELISA) and read the optical density.

b) measure the radioactivity (RIA).

2.9—Measure the quantity of TNF produced by the monocytes.

2.10—Calculate the value of inhibition of the TNF production.

3—RESULTS

Value of inhibition of the α-TNF production by the monocytes treated with anti-direction oligonucleotides was $$\left(1 - \frac{V/ml \text{ in the presence of oligos}}{V/ml \text{ in the absence of oligos}}\right) \times 100 = 63.5 \pm 9$$

Various modifications of the products and method may be made without departing from the spirit or scope thereof and it is to be understood that the invention is intended to be limited only as defined in the appended claims.

---

What is claimed is:

1. A sequence of anti-direction, anti-messenger RNA oligonucleotides of α-TNF characterized in that it possesses the structure of the formula

5'TCA TGG TGT CCT TTG CAG-N 3'   (SEQ ID NO:1)

wherein N is a hydrogen atom,
or a sequence of the formula 5' CC 3',
or a sequence of the formula 5' CC TCA TGC TTT CAG TAG 3', and wherein some of the phosphate groups are in free form, in alkylated form, in thiolate or dithiolate form, or in the form of poly-L-lysine derivative.

2. A process for the preparation of the oligonucleotide sequence of claim 1 comprising immobilizing on a support S the first nucleotide in position 3' of the chain to be synthesized of the formula

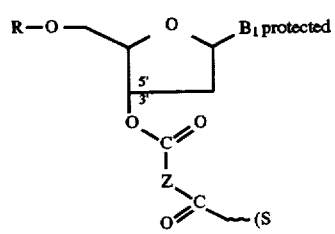

wherein S is the support, Z is a hydrocarbon of 2 to 20 carbon atoms, $B_1$ is a purine and pyrimidine base corresponding to the first nucleotide, the amine function of which is protected, and R is a protector group, deblocking the hydroxyl in position 5' with an acid reagent to obtain a compound of the formula

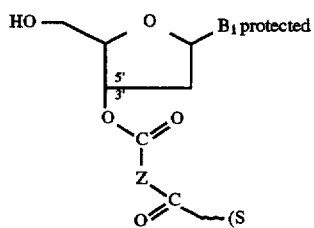

wherein S, Z and $B_1$ have the above definitions, reacting the latter with the monomer of the second nucleotide of the formula

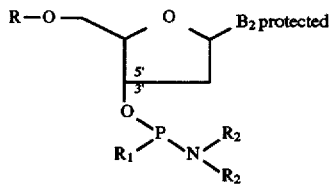

wherein R has the above definitions, $B_2$ is a purine or pyrimidine base corresponding to the second nucleotide, the amine function of which is protected, $R_1$ is alkyl or —$OR'_1$ or $SR'_1$ in which $R'_1$ is a protector group and $R_2$ is a protector group to obtain a product of the formula

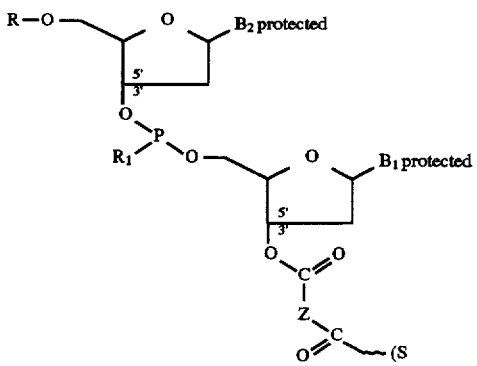

wherein S, R, $R_1$, $B_1$ and $B_2$ have the above definitions, oxidizing the latter product to obtain a product of the formula

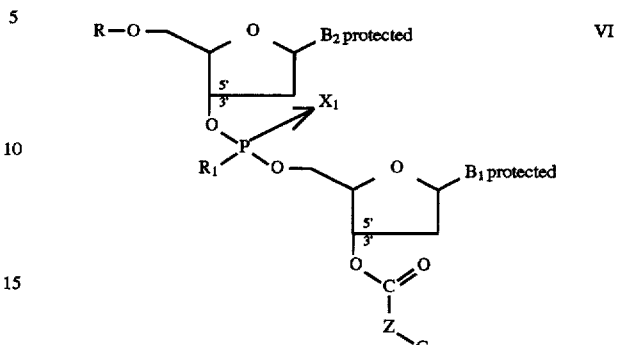

wherein S, R, $R_1$, $B_1$, $B_2$ and Z have the above definitions and $X_1$ is oxygen or sulfur, then, reacting the product of formula VI with the product of formula IV and oxidizing, and repeating for addition of each new nucleotide until the desired chain formation is obtained to obtain a product of the formula

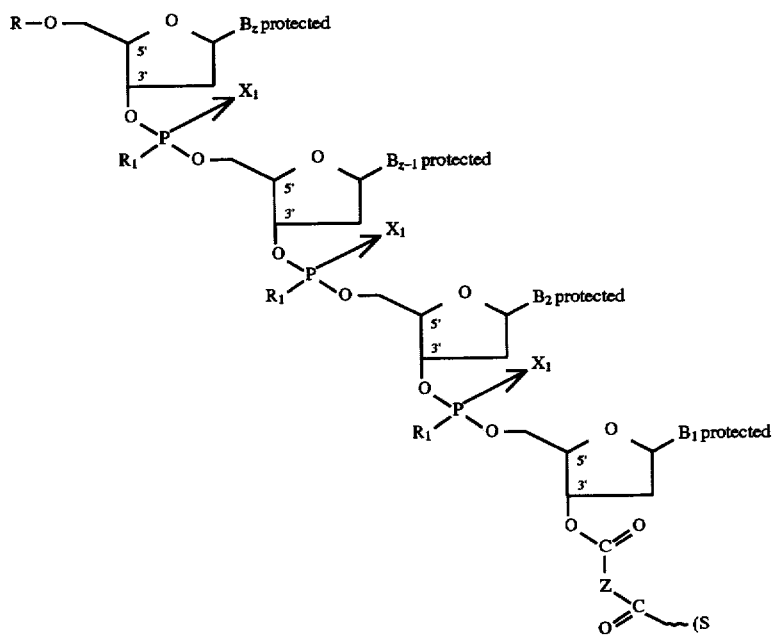

VII wherein S, R, $R_1$, $B_1$, $B_2$, $X_1$ and Z have the above definitions and $B_z$ is the last nucleotide of the sequence, deprotecting the oligo-nucleotide, separation from the support and purifying the product of formula I.

3. The process of claim 2 wherein the deblocking of the hydroxyl in position 5' of the product of formula II is effected with an acid reagent, the coupling reaction of the product of formula III with the product of formula IV is activated by tetrazole in acetonitrile, the oxidation of the phosphite of formula V into phosphate of formula VI is effected with iodine in solution in a water/lutidine tetrahydrofuran mixture or in a water/pyridine/tetrahydrofuran mixture, the oxidation of the phosphite of formula V to obtain the sulfated form VI is effected with sulfur in solution in a mixture of carbon sulfide, anhydrous pyridine and anhydrous triethylamine, at the end of the synthesis, the deprotection of the terminal hydroxyl group in position 5' is effected with an acid, the deprotection of the oligonucleotide of formula VII is effected with concentrated ammonium hydroxide by moderately heating the reaction medium.

4. The process of claim 3 wherein the acid deblocking and deprotecting agent is acetic acid or dichloroacetic acid or trichloroacetic acid.

5. An oligonucleotide sequence of claim 1 wherein N is CC of the formula

5'                                3'
5' TCA TGG TGT CCT TTG CAG CC 3' (Seq. ID No. 3)
1                                20 wherein all or some of the phosphate groups are in free form, in alkylated form, in thiolate or dithiolate form, or in the form of a poly L-lysine derivative.

6. An oligonucleotide sequence of claim 1 wherein N is zero of the formula

5'                                3'
5' TCA TGG TGT CCT TTG CAG 3' (Seq. ID No. 4)
1                                18 wherein all or some of the phosphate groups are in free form, alkylated form, in thiolate or dithiolate form, or in the form of a poly L-lysine derivative.

7. An oligonucleotide sequence of claim 1 wherein N is the sequence SEQ ID No. 2 of the formula 5'                                3'
5' TCA TGG TGT CCT TTG CAG CC TCA TGC TTT CAG TAG 3'
1                                35

(Seq. ID No. 5)

wherein all or some of the phosphate groups are in free form, alkylated form, in thiolate or dithiolate form, or in the form of a poly L-lysine derivative.

8. A composition for reducing the production of α-TNF comprising an effective amount of a sequence of claim 1 to reduce the production of α-TNF and an inert pharmaceutical carrier.

9. A method of reducing the production of α-TNF in a cultured human cell comprising providing to a cultured human cell an amount of the oligonucleotide of claim 1 which inhibits production of α-TNF by the cell.

* * * * *